(12) United States Patent
Kagawa et al.

(10) Patent No.: US 9,656,970 B2
(45) Date of Patent: May 23, 2017

(54) 5-(TRIFLUOROMETHYL)PYRIMIDINE DERIVATIVES AND METHOD FOR PRODUCING SAME

(71) Applicant: TOSOH F-TECH, INC., Yamaguchi (JP)

(72) Inventors: Takumi Kagawa, Yamaguchi (JP); Daiki Shigehiro, Yamaguchi (JP); Kosuke Kawada, Yamaguchi (JP)

(73) Assignee: TOSOH F-TECH, INC., Yamaguchi (JP)

( * ) Notice: Subject to any disclaimer, the term of this patent is extended or adjusted under 35 U.S.C. 154(b) by 0 days.

(21) Appl. No.: 15/125,112

(22) PCT Filed: Apr. 23, 2015

(86) PCT No.: PCT/JP2015/062410
§ 371 (c)(1),
(2) Date: Sep. 9, 2016

(87) PCT Pub. No.: WO2015/170600
PCT Pub. Date: Nov. 12, 2015

(65) Prior Publication Data
US 2016/0376241 A1    Dec. 29, 2016

(30) Foreign Application Priority Data

May 8, 2014   (JP) ................. 2014-096891
May 26, 2014  (JP) ................. 2014-108041
Jun. 16, 2014  (JP) ................. 2014-123375
Jun. 18, 2014  (JP) ................. 2014-125381

(51) Int. Cl.
*C07D 239/52*   (2006.01)
*C07D 239/34*   (2006.01)
*C07D 239/38*   (2006.01)

(52) U.S. Cl.
CPC ......... *C07D 239/52* (2013.01); *C07D 239/34* (2013.01); *C07D 239/38* (2013.01)

(58) Field of Classification Search
CPC .................................................... C07D 239/52
USPC ........................................ 544/309, 315, 319
See application file for complete search history.

(56) References Cited

U.S. PATENT DOCUMENTS

| 2005/0101620 A1 | 5/2005 | Kath et al. |
| 2008/0175794 A1 | 7/2008 | Caldwell et al. |
| 2011/0251222 A1 | 10/2011 | Lucking et al. |
| 2012/0157427 A1 | 6/2012 | Baker-Glenn et al. |

FOREIGN PATENT DOCUMENTS

JP     2007107228 A    4/2007

OTHER PUBLICATIONS

Masashi et al., Machine Translation of JP 2004-107228, 32 pages (2004).*
Sharad Verma et al., "Substituted aminobenzimidazole pyrimides as cyclin-dependent kinase inhibitors", Bioorganic & Medical Chemistry Letters, 2005, available online www.sciencedirect.com.
English translation of International Search Report dated Aug. 4, 2016 for corresponding PCT Application No. PCT/JP2015/062410.

* cited by examiner

*Primary Examiner* — Deepak Rao
(74) *Attorney, Agent, or Firm* — Kinney & Lange, P.A.

(57) ABSTRACT

Provided are 5-(trifluoromethyl)pyrimidine derivatives useful as intermediates for pharmaceuticals and agrochemicals and as intermediates for electronic materials and methods for producing the same. 2,4-dichloro-5-(trifluoromethyl)pyrimidine is reacted with 2,2,2-trifluoroethanol, benzyl alcohol, or benzenethiol to obtain the intended 2-(2,2,2-trifluoroethoxy)-4-chloro-5-(trifluoromethyl)pyrimidine, 2-benzyloxy-4-chloro-5-(trifluoromethyl)pyrimidine, 2,4-bis(2,2,2-trifluoroethoxy)-5-(trifluoromethyl)pyrimidine, or 2-chloro-4-phenylthio-5-(trifluoromethyl)pyrimidine.

7 Claims, No Drawings

5-(TRIFLUOROMETHYL)PYRIMIDINE DERIVATIVES AND METHOD FOR PRODUCING SAME

TECHNICAL FIELD

The present invention relates to novel 5-(trifluoromethyl)pyrimidine derivatives and methods for producing the same. 5-(trifluoromethyl)pyrimidine derivatives such as 2,4-bis(2,2,2-trifluoroethoxy)-5-(trifluoromethyl)pyrimidine, 2-benzyloxy-4-chloro-5-(trifluoromethyl)pyrimidine, 2-(2,2,2-trifluoroethoxy)-4-chloro-5-(trifluoromethyl)pyrimidine, and 2-chloro-5-phenylthio-5-(trifluoromethyl)pyrimidine are compounds useful as raw materials for synthesis of various pharmaceuticals, agrochemicals, and electronic materials.

BACKGROUND ART

The 5-(trifluoromethyl)pyrimidine derivatives and methods for producing the same according to the present invention have hitherto been unknown.

As for analogues of 2-(2,2,2-trifluoroethoxy)-4-chloro-5-(trifluoromethyl)pyrimidine and 2-benzyloxy-4-chloro-5-(trifluoromethyl)pyrimidine according to the present invention, 2-methoxy-4-chloro-5-(trifluoromethyl)pyrimidine has been known and there is a known method in which 2,4-dichloro-5-(trifluoromethyl)pyrimidine and methanol are reacted in the presence of triethylamine to give a mixture of 2-methoxy-4-chloro-5-(trifluoromethyl)pyrimidine and 2-chloro-4-methoxy-5-(trifluoromethyl)pyrimidine and the mixture is purified by silica gel column chromatography to obtain the intended 2-methoxy-4-chloro-5-(trifluoromethyl)pyrimidine (see Patent Document 1, for example).

However, there has been a problem in that when the method described in Patent Document 1 is used in an attempt to produce 2-(2,2,2-trifluoroethoxy)-4-chloro-5-(trifluoromethyl)pyrimidine according to the present invention, the intended 2-(2,2,2-trifluoroethoxy)-4-chloro-5-(trifluoromethyl)pyrimidine is not formed. There have also been problems in that: when the method is used in an attempt to produce 2-benzyloxy-4-chloro-5-(trifluoromethyl)pyrimidine, the intended 2-benzyloxy-4-chloro-5-(trifluoromethyl)pyrimidine is not formed; and with the use of a known method using a metal salt of an alcohol, in particular a method in which a lithium salt of benzyl alcohol and 2,4-dichloro-5-(trifluoromethyl)pyrimidine are reacted in a tetrahydrofuran solvent, the resulting product is a mixture of the intended 2-benzyloxy-4-chloro-5-(trifluoromethyl)pyrimidine and its regioisomer, 2-chloro-4-benzyloxy-5-(trifluoromethyl)pyrimidine (intended product/isomer=73/27), and separation and purification by a process such as silica gel column chromatography must be performed to obtain the intended product.

On the other hand, as an analogue of 2,4-bis(2,2,2-trifluoroethoxy)-5-(trifluoromethyl)pyrimidine according to the present invention, 2,4-dichloro-5-(trifluoromethyl)pyrimidine (which may hereinafter be abbreviated as "CFP") has been known and there is a known method in which the latter compound is substituted at the 2-position and 4-position of the pyrimidine ring by various substituents to produce candidate drugs for pharmaceuticals (see Patent Document 2, for example).

However, highly selective introduction of various substituents at the 2-position or 4-position with CFP is difficult by conventional methods, according to which the resulting product is a mixture of a 2-substituted product and a 4-substituted product. There has thus been a problem in that separation and purification by a process such as silica gel column chromatography must be performed to obtain the intended product of high purity.

Furthermore, as for an analogue of 2-chloro-4-phenylthio-5-(trifluoromethyl)pyrimidine according to the present invention, 2-chloro-4-methylthio-5-(trifluoromethyl)pyrimidine has been known and is obtained by a reaction between 2,4-dichloro-5-(trifluoromethyl)pyrimidine and sodium thiomethoxide (see Patent Document 1, for example).

However, the method described in Patent Document 1 has problems in that it is a method involving purification by silica gel column chromatography of the mixture of 2-chloro-5-methylthio-5-(trifluoromethyl)pyrimidine and 2-methylthio-4-chloro-5-(trifluoromethyl)pyrimidine obtained by the reaction and is required to be further improved for use as an industrial production method, and in that the yield is 28%, which is low.

PRIOR ART DOCUMENT

Patent Document

Patent Document 1: National Publication of International Patent Application No. 2008-528613
Patent Document 2: Japanese Patent No. 4842816

SUMMARY OF THE INVENTION

Problems to be Solved by the Invention

The present invention is directed to providing: 5-(trifluoromethyl)pyrimidine derivatives such as 2-(2,2,2-trifluoroethoxy)-4-chloro-5-(trifluoromethyl)pyrimidine, 2-benzyloxy-4-chloro-5-(trifluoromethyl)pyrimidine, 2,4-bis(2,2,2-trifluoroethoxy)-5-(trifluoromethyl)pyrimidine, and 2-chloro-4-phenylthio-5-(trifluoromethyl)pyrimidine which are expected as introducers of a 5-(trifluoromethyl)pyrimidine skeleton; and methods for producing the same.

Means for Solving the Problems

More specifically, the present invention provides the following.

[1] A 5-(trifluoromethyl)pyrimidine derivative represented by the following general formula (1):

[Formula 1]

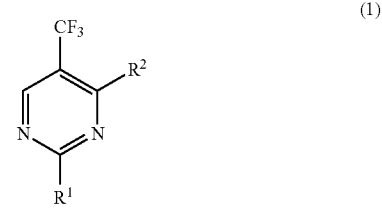

wherein
$R^1$ is a 2,2,2-trifluoroethoxy group and $R^2$ is a chlorine atom or a 2,2,2-trifluoroethoxy group, or
$R^1$ is a benzyloxy group and $R^2$ is a chlorine atom, or
$R^1$ is a chlorine atom and $R^2$ is a phenylthio group.

[2] The 5-(trifluoromethyl)pyrimidine derivative according to [1], wherein, in the general formula (1), $R^1$ is a 2,2,2-trifluoroethoxy group and $R^2$ is a chlorine atom or a 2,2,2-trifluoroethoxy group, the 5-(trifluoromethyl)pyrimidine derivative being represented by the following general formula (2):

[Formula 2]

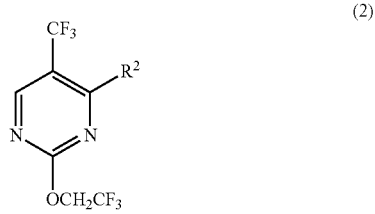
(2)

[3] The 5-(trifluoromethyl)pyrimidine derivative according to [1] or [2], wherein, in the general formula (1), $R^1$ and $R^2$ are each a 2,2,2-trifluoroethoxy group, the 5-(trifluoromethyl)pyrimidine derivative being represented by the following formula (3):

[Formula 3]

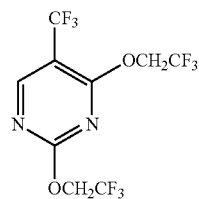
(3)

[4] A method for producing the 5-(trifluoromethyl)pyrimidine derivative according to [2] or [3], the method comprising reacting 2,4-dichloro-5-(trifluoromethyl)pyrimidine with a metal 2,2,2-trifluoroethoxide.

[5] A method for producing 2-(2,2,2-trifluoroethoxy)-4-chloro-5-(trifluoromethyl)pyrimidine represented by the formula (2) according to [2], the method comprising reacting 2,4-dichloro-5-(trifluoromethyl)pyrimidine with a metal salt of 2,2,2-trifluoroethanol.

[6] The method for producing 2-(2,2,2-trifluoroethoxy)-4-chloro-5-(trifluoromethyl)pyrimidine according to [5], wherein the metal salt is a lithium salt, a sodium salt, or a potassium salt.

[7] The 5-(trifluoromethyl)pyrimidine derivative according to [1], wherein, in the general formula (1), $R^1$ is a benzyloxy group and $R^2$ is a chlorine atom, the 5-(trifluoromethyl)pyrimidine derivative being represented by the following formula (4):

[Formula 4]

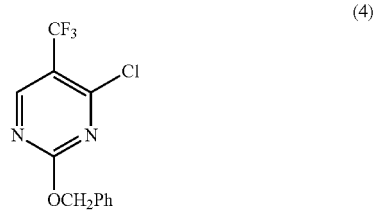
(4)

[8] A method for producing the 5-(trifluoromethyl)pyrimidine derivative according to [7], the method comprising reacting 2,4-dichloro-5-(trifluoromethyl)pyrimidine with a metal salt of benzyl alcohol in a mixed solvent of tetrahydrofuran and hexane.

[9] The method for producing the 5-(trifluoromethyl)pyrimidine derivative according to [8], wherein the metal salt is a lithium salt, a sodium salt, or a potassium salt.

[10] The 5-(trifluoromethyl)pyrimidine derivative according to [1], wherein, in the general formula (1), $R^1$ is a chlorine atom and $R^2$ is a substituted phenylthio group, the 5-(trifluoromethyl)pyrimidine derivative being represented by the following general formula (5):

[Formula 5]

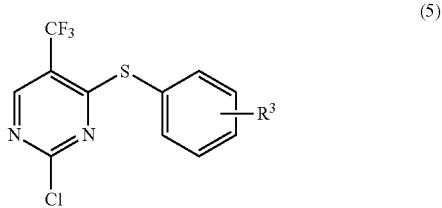
(5)

wherein $R^3$ represents a hydrogen atom or a methyl group.

[11] A method for producing 2-chloro-5-(trifluoromethyl)pyrimidine represented by the general formula (5) according to [10], the method comprising reacting 2,4-dichloro-5-(trifluoromethyl)pyrimidine with a metal salt of an aromatic thiols represented by the following general formula (6):

[Formula 6]

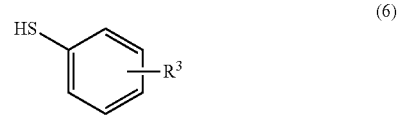
(6)

wherein $R^3$ is the same as defined in the formula (5).

[12] The method for producing the 2-chloro-5-(trifluoromethyl)pyrimidine derivative according to [11], wherein the metal salt is a lithium salt, a sodium salt, or a potassium salt.

Advantageous Effects of the Invention

According to the present invention, there are provided: 5-(trifluoromethyl)pyrimidine derivatives such as 2,4-bis(2,2,2-trifluoroethoxy)-5-(trifluoromethyl)pyrimidine, 2-(2,2,2-trifluoroethoxy)-4-chloro-5-(trifluoromethyl)pyrimidine, 2-benzyloxy-4-chloro-5-(trifluoromethyl)pyrimidine, and 2-chloro-4-phenylthio-5-(trifluoromethyl)pyrimidine which are novel as raw materials for synthesis of pharmaceuticals and agrochemicals; and methods for producing the same.

It is expected that 2-(2,2,2-trifluoroethoxy)-4-chloro-5-(trifluoromethyl)pyrimidine according to the present invention allows introduction of another substituent at the 4-position and that a 2- and 4-substituted 5-(trifluoromethyl)pyrimidine derivative is derived by further substituting the 2,2,2-trifluoroethoxy group at the 2-position by some substituent.

It is also expected that 2-benzyloxy-4-chloro-5-(trifluoromethyl)pyrimidine according to the present invention allows introduction of another substituent at the 4-position and that a 2- and 4-substituted 5-(trifluoromethyl)pyrimidine derivative can be produced by further deprotecting the benzyloxy group at the 2-position through hydrogenation reaction or the like or substituting the benzyloxy group at the 2-position by some substituent.

It is further expected that 2-chloro-4-phenylthio-5-(trifluoromethyl)pyrimidine according to the present invention allows introduction of another substituent at the 2-position and that a 2- and 4-substituted 5-(trifluoromethyl)pyrimidine derivative is derived by further oxidizing the aromatic thio group at the 4-position and then substituting the oxidized group by some substituent.

MODE FOR CARRYING OUT THE INVENTION

Hereinafter, the present invention will be described in detail.

2,4-dichloro-5-(trifluoromethyl)pyrimidine used as a raw material in the present invention can be prepared, for example, industrially-available 5-(trifluoromethyl)uracil with phosphorus oxychloride or the like by dehydration and chlorination.

The method for producing 2-(2,2,2-trifluoroethoxy)-4-chloro-5-(trifluoromethyl)pyrimidine according to the present invention will now be described.

It is recommended that 2,2,2-trifluoroethanol used for the production of 2-(2,2,2-trifluoroethoxy)-4-chloro-5-(trifluoromethyl)pyrimidine according to the present invention be used in an amount of 1.0 mole to 1.5 moles based on the mole of 2,4-dichloro-5-(trifluoromethyl)pyrimidine subjected to the reaction.

Specific examples of a metal reagent applicable to preparation of the metal salt of 2,2,2-trifluoroethanol which is used for the production of 2-(2,2,2-trifluoroethoxy)-4-chloro-5-(trifluoromethyl)pyrimidine according to the present invention include lithium metal, sodium metal, potassium metal, lithium hydride, sodium hydride, potassium hydride, n-butyllithium, tert-butyllithium, lithium diisopropylamide, lithium hexamethyldisilazide, sodium hexamethyldisilazide, and potassium hexamethyldisilazide. It is recommended that the metal reagent be used in an amount of 0.7 moles to 1.0 mole besed on the mole of benzyl alcohol subjected to the reaction. A commercially-available solution diluted to a given concentration with any of various solvents may also be used as the metal reagent.

Specific examples of the solvent applicable to the production of 2-(2,2,2-trifluoroethoxy)-4-chloro-5-(trifluoromethyl)pyrimidine according to the present invention include: ether solvents such as diethyl ether, diisopropyl ether, methyl tert-butyl ether, tetrahydrofuran, and methyl cyclopentyl ether; aromatic solvents such as benzene, toluene, ethylbenzene, mesitylene, and cumene; and aliphatic hydrocarbon solvents such as n-pentane, n-hexane, and cyclohexane. It is recommended that the solvent be used in an amount of 5 parts by weight to 40 parts by weight besed on the weight of 2,4-dichloro-5-(trifluoromethyl)pyrimidine subjected to the reaction. A mixture of two or more of the above solvents may also be used.

The reaction temperature and reaction time applicable to the production of 2-(2,2,2-trifluoroethoxy)-4-chloro-5-(trifluoromethyl)pyrimidine according to the present invention vary depending on the type of the metal reagent used, the type of the solvent, and the substrate concentration. In general, the reaction is completed when performed in a temperature range of −80 to 65° C. for 4 to 48 hours.

Post-treatment subsequent to the production of 2-(2,2,2-trifluoroethoxy)-4-chloro-5-(trifluoromethyl)pyrimidine according to the present invention is possible by means of a well-known technique. For example, the reactant may be obtained as a liquid, through was quenched with a saturated aqueous ammonium chloride solution, extracted with a solvent such as dichloromethane, dried over sodium sulfate, filtrated, and concentrated, and purification of the crude product by distillation where necessary.

The method for producing 2-benzyloxy-4-chloro-5-(trifluoromethyl)pyrimidine according to the present invention will now be described.

It is recommended that benzyl alcohol used for the production of 2-benzyloxy-4-chloro-5-(trifluoromethyl)pyrimidine according to the present invention be used in an amount of 1.0 to 1.5 moles per mole of 2,4-dichloro-5-(trifluoromethyl)pyrimidine subjected to the reaction.

Specific examples of a metal reagent applicable to preparation of the metal salt of benzyl alcohol which is used for the production of 2-benzyloxy-4-chloro-5-(trifluoromethyl)pyrimidine according to the present invention include lithium metal, sodium metal, potassium metal, lithium hydride, sodium hydride, potassium hydride, n-butyllithium, tert-butyllithium, lithium diisopropylamide, lithium hexamethyldisilazide, sodium hexamethyldisilazide, and potassium hexamethyldisilazide. It is recommended that the metal reagent be used in an amount of 0.7 to 1.0 mole based on the mole of benzyl alcohol subjected to the reaction. The combination of benzyl alcohol and the above metal reagent yields a lithium salt, sodium salt, or potassium salt of benzyl alcohol, and the salt is subjected to the reaction. One metal reagent may be used alone or two or more metal reagents may be used in combination. In addition, a commercially-available solution of metal reagents diluted to some concentration with any of various solvents may be used alone, or two or more such solutions may be used in combination, as the metal reagent.

The mixed solvent of tetrahydrofuran and hexane used for production of 2-benzyloxy-4-chloro-5-(trifluoromethyl)pyrimidine according to the present invention is applicable when the ratio, tetrahydrofuran/hexane, is in the range of ½ (vol/vol) to ⅛ (vol/vol). If the amount of hexane used is smaller, the selectivity may decrease, while the use of too large the amount of hexane, the yield of the product decrease by the precipitation of the metal salt of benzyl alcohol.

It is recommended that the mixed solvent of tetrahydrofuran and hexane used for production of 2-benzyloxy-4-chloro-5-(trifluoromethyl)pyrimidine according to the present invention be used in an amount of 5 to 40 parts by weight based on the weight of 2,4-dichloro-5-(trifluoromethyl)pyrimidine subjected to the reaction.

The reaction temperature and reaction time applicable to the production of 2-benzyloxy-4-chloro-5-(trifluoromethyl)pyrimidine according to the present invention vary depending on the type of the metal reagent used, the composition of the mixed solvent, and the substrate concentration. In general, the reaction is completed when performed in a temperature range of −80 to 65° C. for 4 to 48 hours.

Post-treatment subsequent to the production of 2-benzyloxy-4-chloro-5-(trifluoromethyl)pyrimidine according to the present invention is possible by means of a well-known technique. For example, the reactant may be obtained as a solid, through was quenched with a saturated aqueous ammonium chloride solution, extracted with a solvent such as dichloromethane, dried over sodium sulfate, filtrated, and concentrated, and the purification of the crude product by recrystallization where necessary.

The method for producing 2,4-bis(2,2,2-trifluoroethyl)-5-(trifluoromethyl)pyrimidine according to the present invention will now be described.

An available method for producing TFEFP according to the present invention is to produce TFEFP by reaction of 2,4-dichloro-5-(trifluoromethyl)pyrimidine (CFP) and a metal 2,2,2-trifluoroethoxide.

As one example of the production method, metal salt of 2,2,2-trifluoroethanol which was prepared 2,2,2-trifluoroethanol with organometal or a metal hydride in situ was reacted with CFP to produce TFEFP. As another example, the isolated metal salt of 2,2,2-trifluoroethanol was reacted with CFP to produce TFEFP.

CFP used as a raw material in the method for producing TFEFP according to the present invention is an industrially-available material and is prepared, for example, by a method in which 5-(trifluoromethyl)uracil is dehydrated and chlorinated with phosphorus oxychloride or the like.

Specific examples of the metal salt of 2,2,2-trifluoroethanol applicable to the production according to the present invention include lithium 2,2,2-trifluoroethoxide, sodium 2,2,2-trifluoroethoxide, and potassium 2,2,2-trifluoroethoxide. It is recommended that the metal salt be used in an amount of 2.0 moles or more, preferably in an amount of 2.2 to 3.0 moles, based on the mole of CFP subjected to the reaction. It is preferable to prepare the metal salt of 2,2,2-trifluoroethanol within the system prior to the reaction with CFP, and it is recommended to perform the preparation in a temperature range of −80° C. to room temperature by dissolving 2,2,2-trifluoroethanol in a solvent that is inactive in the reaction and using an organometal or metal hydride such as lithium hydride, sodium hydride, potassium hydride, methyllithium, n-butyllithium, tert-butyllithium, lithium diisopropylamide, lithium hexamethyldisilazide, sodium hexamethyldisilazide, or potassium hexamethyldisilazide in an amount of 0.9 moles to 1.0 mole based on the mole of 2,2,2-trifluoroethanol.

The solvent applicable to the production according to the present invention is not particularly limited which the solvent is inactive in the reaction. Specific examples of the solvent include: ether solvents such as diethyl ether, diisopropyl ether, tetrahydrofuran, cyclopentyl methyl ether, and methyl tert-butyl ether; and aliphatic hydrocarbon solvents such as n-pentane, n-hexane, and cyclohexane. It is recommended that the solvent be used in an amount of 5 to 50 parts by weight based on the weight of CFP subjected to the reaction. These solvents may be used alone or may be used as a mixture.

The reaction temperature and reaction time in the method for producing TFEFP according to the present invention vary depending on the type of the metal salt of 2,2,2-trifluoroethanol and the type and amount of the solvent. In general, the reaction can be completed when performed in a temperature range of −80 to 100° C. for 1 to 24 hours.

Post-treatment subsequent to the reaction according to the present invention is not particularly limited to a commonly-known technique is used. For example, the intended TFEFP can be obtained through neutralization with a saturated aqueous ammonium chloride solution, concentration, extraction with dichloromethane, drying, filtration, and concentration. Purification by silica gel treatment, distillation or the like may further be performed.

The method for producing 2-chloro-4-phenylthio-5-(trifluoromethyl)pyrimidine according to the present invention will now be described.

Specific examples of the aromatic thiol (2), represented by the general formula (2), which is applicable to the production of the 2-chloro-5-(trifluoromethyl)pyrimidine derivative (1) according to the present invention include benzenethiol, 2-methylbenzenethiol, 3-methylbenzenethiol, and 4-methylbenzenethiol. It is recommended that the aromatic thiol (2) be used in an amount of 0.9 moles to 1.3 moles based on the mole of 2,4-dichloro-5-(trifluoromethyl) pyrimidine subjected to the reaction.

As for metal salt of an aromatic thiols used for the production of the 2-chloro-5-(trifluoromethyl)pyrimidine derivative (1) according to the present invention, a commercially-available a metal salt of aromatic thiols may be used by itself or, where necessary, a metal salt of aromatic thiols may be prepared within the system. Specific examples of a metal reagent applicable to the preparation within the system include lithium metal, sodium metal, potassium metal, lithium hydride, sodium hydride, potassium hydride, n-butyllithium, tert-butyllithium, lithium diisopropylamide, lithium hexamethyldisilazide, sodium hexamethyldisilazide, and potassium hexamethyldisilazide. It is recommended that the metal reagent be used in an amount of 0.8 moles to 1.0 mole based on the mole of the aromatic thiol subjected to the reaction. A commercially-available solution of metal reagents diluted to some concentration with any of various solvents may also be used as the metal reagent.

The solvent applicable to the production of the 2-chloro-5-(trifluoromethyl)pyrimidine derivative (1) according to the present invention is not particularly limited which the solvent is inactive in the reaction. Specific examples of the solvent include: ether solvents such as diethyl ether, diisopropyl ether, cyclopentyl methyl ether, and tetrahydrofuran; aromatic hydrocarbon solvents such as benzene, toluene, ethylbenzene, cumene, and mesitylene; and aliphatic hydrocarbon solvents such as pentane, n-hexane, cyclohexane, and n-pentane. It is recommended that the solvent be used in an amount of 5 parts by weight to 40 parts by weight based on the weight of 2,4-dichloro-5-(trifluoromethyl)pyrimidine subjected to the reaction. In addition, where necessary, two or more solvents may be mixed and used.

The reaction temperature and reaction time applicable to the production of the 2-chloro-5-(trifluoromethyl)pyrimidine derivative (1) according to the present invention vary depending on the type of the metal reagent used, the composition of the solvent, and the substrate concentration. In general, the reaction is completed when performed in a temperature range of −40 to 50° C. for 4 to 48 hours.

Post-treatment subsequent to the production of the 2-chloro-5-(trifluoromethyl)pyrimidine derivative (1) according to the present invention is possible by means of a well-known technique. For example, a crude product may be obtained as a solid through neutralization with a saturated aqueous ammonium chloride solution, extraction with a solvent such as dichloromethane, drying over sodium sulfate, filtration, and concentration, and the crude product may be purified by recrystallization where necessary.

EXAMPLES

Hereinafter, the present invention will be specifically described with reference to examples; however, the present invention is not limited only to these examples. For analyses, the following apparatuses were used.

$^1$H-NMR, $^{19}$F-NMR, $^{13}$C-NMR: AVANCE II 400, manufactured by BRUKER CORPORATION GC-MS: GCMS-QP2010Plus, manufactured by Shimadzu Corporation Element analysis: CHN Coder MT-6, manufactured by Yanaco Technical Science Co., Ltd.

Example 1

Preparation of 2-(2,2,2-trifluoroethoxy)-4-chloro-5-(trifluoromethyl)pyrimidine (7)

[Formula 7]

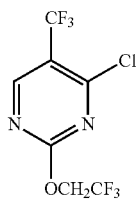

(7)

To a 2000 mL four-necked round-bottom flask equipped with a stirrer bar, 2,2,2-trifluoroethanol (40.12 g, 0.401 mol) and tetrahydrofuran (1475 mL) were added under nitrogen. After cooling to −20° C., n-butyllithium (1.6 M hexane solution, 250 mL, 0.400 mol) was added, followed by stirring at the same temperature for 30 minutes. Subsequently, 2,4-dichloro-5-(trifluoromethyl)pyrimidine (CFP, 86.73 g, 0.400 mol) was added dropwise over 30 minutes, followed by further stirring at the same temperature for 30 minutes and then the reaction mixture was stirred at room temperature for 6 hours.

After the reaction was completed, the reaction mixture was quenched with saturated aqueous sodium chloride solution (600 mL×3 times) and then concentrated under reduced pressure to obtain crude product (119.33 g) as a yellow liquid. At this stage, the conversion of CFP and yield of the product were determined by $^{19}$F-NMR of the crude product using hexafluorobenzene as an internal standard, and it was found that the intended 2-(2,2,2-trifluoroethoxy)-4-chloro-5-(trifluoromethyl)pyrimidine (7) was produced at a conversion of 97% and in a yield of 80%. As for by-products, an isomer, 2-chloro-4-(2,2,2-trifluoroethoxy)-5-(trifluoromethyl)pyrimidine, was contained in an amount of 4% in a yield, and 2,4-bis(2,2,2-trifluoroethoxy)-5-(trifluoromethyl)pyrimidine as an overreaction product was contained in an amount of 10% in a yield.

Furthermore, the crude product was purified by rectification distillation under reduced pressure using a packed column (Kiriyama Pac, 10 plates, 20 mm ID×250 mmL) to be obtained purified 2-(2,2,2-trifluoroethoxy)-4-chloro-5-(trifluoromethyl)pyrimidine (7) as a colorless liquid (70.21 g, purity=97.0%, yield=61%).

$^1$H-NMR (CDCl$_3$, 400 MHz) δ 8.78 (d, J=0.8 Hz, 1H), 4.89 (q, J=8.0 Hz, 2H).

$^{19}$F-NMR (CDCl$_3$, 376 MHz) δ −63.72.

$^{13}$C-NMR (CDCl$_3$, 100 MHz) δ 164.69, 161.84, 158.98 (q, J=5.0 Hz), 122.80 (q, J=277.2 Hz), 122.04 (q, J=270.3 Hz), 119.13 (q, J=32.6 Hz), 64.71 (q, J=37.0 Hz).

GC-MS (m/z) 280 (34, M$^+$), 261 (34), 225 (32), 211 (91), 182 (100), 155 (47), 147 (32), 120 (31), 83 (69).

Element Analysis

Calculated: carbon (29.97%), hydrogen (1.08%), nitrogen (9.98%)

Measured: carbon (29.92%), hydrogen (1.08%), nitrogen (9.96%)

Example 2

Preparation of 2-(2,2,2-trifluoroethoxy)-4-chloro-5-(trifluoromethyl)pyrimidine (7)

To a 50 mL eggplant-shaped flask equipped with a stirrer bar, 2,2,2-trifluoroethanol (0.65 g, 6.54 mmol) and tetrahydrofuran (4 mL) were added under nitrogen stream. After cooling to −20° C., n-butyllithium (1.6 M hexane solution, 2.95 mL, 4.71 mmol) was added, followed by stirring at the same temperature for 30 minutes. Subsequently, at the same temperature, n-hexane (10 mL) was added and then 2,4-dichloro-5-(trifluoromethyl)pyrimidine (CFP, 1.00 g, 4.61 mmol) was added. The reaction mixture was followed by further stirring at the same temperature for 30 minutes and then stirred at room temperature for 3 hours.

After the reaction was completed, the reactant was quenched with saturated aqueous ammonium chloride solution (10 mL), concentrated to remove of tetrahydrofuran under reduced pressure, extraced with dichloromethane (10 mL×3 times), combined the organic layers and dried over sodium sulfate, filtrated, and then concentration, to give a crude product of 2-(2,2,2-trifluoroethoxy)-4-chloro-5-(trifluoromethyl)pyrimidine (7) as a pale yellow liquid (1.34 g). At this stage, the conversion of CFP and yield of the product were determined by $^{19}$F-NMR of the crude product using hexafluorobenzene as an internal standard, and it was found that the intended 2-(2,2,2-trifluoroethoxy)-4-chloro-5-(trifluoromethyl)pyrimidine (7) was produced at a conversion of 97% and a yield of 84%. As the by-products ofthe isomer, 2-chloro-4-(2,2,2-trifluoroethoxy)-5-(trifluoromethyl)pyrimidine, was contained in an amount of 2% in a yield and 2,4-bis(2,2,2-trifluoroethoxy)-5-(trifluoromethyl)pyrimidine as an overreaction product was contained in an amount of 13% in a yield.

Example 3

Preparation of 2-(2,2,2-trifluoroethoxy)-4-chloro-5-(trifluoromethyl)pyrimidine (7)

To the same reactor as used in Example 2, 2,2,2-trifluoroethanol (0.55 g, 5.53 mmol) and tetrahydrofuran (15 mL) were added. After cooling to −0° C., sodium hydride (60% in oil, 0.20 g, 4.99 mmol) was added, followed by stirring at the same temperature for 30 minutes. Subsequently, after cooling to −20° C., n-hexane (10 mL) was added and then 2,4-dichloro-5-(trifluoromethyl)pyrimidine (1.00 g, 4.61 mmol) was added. The reaction mixture was followed by further stirring at the same temperature for 30 minutes and then by stirring at 0° C. for 16 hours.

After the reaction was completed, the reactant was treated with the same post-treatment process as performed in Example 2 to giving a crude product of 2-(2,2,2-trifluoroethoxy)-4-chloro-5-(trifluoromethyl)pyrimidine (7) (1.37 g). At this stage, the conversion of CFP and yield of the product were determined by $^{19}$F-NMR of the crude product using hexafluorobenzene as an internal standard, and it was found that the intended 2-(2,2,2-trifluoroethoxy)-4-chloro-5-(trifluoromethyl)pyrimidine (7) was produced at a conversion of 99% and a yield of 87%. As the by-products of isomer, 2-chloro-4-(2,2,2-trifluoroethoxy)-5-(trifluoromethyl)pyrimidine was contained in an amount of 1% in a yield and as the overreaction product, 2,4-bis(2,2,2-trifluoroethoxy)-5-(trifluoromethyl)pyrimidine was contained in an amount of 8% in a yield.

Example 4

Preparation of 2-(2,2,2-trifluoroethoxy)-4-chloro-5-(trifluoromethyl)pyrimidine (7)

To the same reactor as used in Example 2, 2,2,2-trifluoroethanol (0.55 g, 5.53 mmol) and tetrahydrofuran (20 mL) were added. After cooling to −40° C., potassium hexamethyldisilazide (1.0 M tetrahydrofuran solution, 4.70 mL, 4.70 mmol) was added, followed by stirring at the same temperature for 30 minutes. Subsequently, 2,4-dichloro-5-(trifluoromethyl)pyrimidine (1.00 g, 4.61 mmol) was added. The reaction mixture was followed by further stirring at the same temperature for 30 minutes and then by stirring at −20° C. for 36 hours.

After the reaction was completed, the reactant was treated followed by the same post-treatment process as performed in Example 2 to give a crude product of 2-(2,2,2-trifluoroethoxy)-4-chloro-5-(trifluoromethyl)pyrimidine (7) (1.33 g). At this stage, the conversion of CFP and yield of the product were determined by $^{19}F$-NMR of the crude product using hexafluorobenzene as an internal standard, and it was found that the intended 2-(2,2,2-trifluoroethoxy)-4-chloro-5-(trifluoromethyl)pyrimidine (7) was produced at a conversion of 99% and a yield of 86%. As the by-products of isomer, 2-chloro-4-(2,2,2-trifluoroethoxy)-5-(trifluoromethyl)pyrimidine was contained in an amount of 2% in a yield and as an overreaction product, 2,4-bis(2,2,2-trifluoroethoxy)-5-(trifluoromethyl)pyrimidine was contained in an amount of 5% in a yield.

Example 5

Preparation of 2,4-bis(2,2,2-trifluoroethoxy)-5-(trifluoromethyl)pyrimidine (3)

[Formula 3]

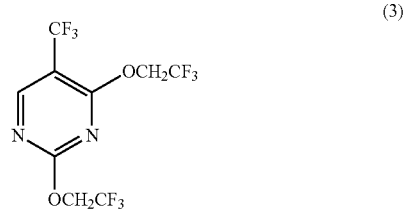

(3)

Placed to a 200 mL eggplant-shaped flask equipped with a stirrer bar, 2,2,2-trifluoroethanol (5.99 g, 59.9 mmol) and tetrahydrofuran (85 mL) were added under a nitrogen stream. After cooling to −20° C., n-butyllithium (1.6 M hexane solution, 34.5 mL, 55.2 mmol) was added, followed by stirring at the same temperature for 30 minutes. Subsequently, CFP (5.00 g, 23.0 mmol) was added to the reaction mixture, followed by stirring at the same temperature for 30 minutes and then by stirring at 40° C. for 24 hours.

After the reaction was completed, the reactant was quenched saturated aqueous ammonium chloride solution (30 mL), concentrated under reduced pressure, extracted with dichloromethane (30 ml×3 times), dried over sodium sulfate, filtrated, and then concentrated under reduced pressure to giving a crude product.

Purification of the crude product by a silica gel bed (10 g, eluent: dichloromethane) gave pure 2,4-bis(2,2,2-trifluoroethoxy)-5-(trifluoromethyl)pyrimidine (3) (7.22 g, 21.0 mmol, yield=91%) as a colorless liquid.

The result of analysis was as follows.

$^{1}H$-NMR (CDCl$_3$, 400 MHz) δ 8.60 (d, J=0.8 Hz, 1H), 4.91 (q, J=4.9 Hz, 2H), 4.85 (q, J=4.8 Hz, 2H).

$^{19}F$-NMR (CDCl$_3$, 376 MHz) δ −63.80, −74.82 (t, J=7.5 Hz), −74.89 (t, J=7.5 Hz).

$^{13}C$-NMR (CDCl$_3$, 100 MHz) δ 167.07, 165.00, 158.38 (q, J=4.7 Hz), 122.99 (q, J=275.8 Hz), 122.74 (q, J=275.6 Hz), 122.28 (q, J=269.4 Hz), 108.05 (q, J=34.7 Hz), 64.39 (q, J=36.7 Hz), 63.39 (q, J=37.2 Hz).

GC-MS (m/z): 344 (M$^+$, 45), 325 (58), 275 (100), 246 (93), 163 (90), 83 (95).

Element Analysis

Calculated: carbon (31.41%), hydrogen (1.46%), fluorine (49.69%), nitrogen (8.14%)

Measured: (31.32%), hydrogen (1.46%), fluorine (49.64%), nitrogen (8.16%)

Example 6

Preparation of 2,4-bis(2,2,2-trifluoroethoxy)-5-(trifluoromethyl)pyrimidine (3)

To the same reactor as used in Example 5, 2,2,2-trifluoroethanol (8.29 g, 82.9 mmol) and sodium hydride (manufactured by Wako Pure Chemical Industries, Ltd., 60% in oil (containing 40% of mineral oil), 3.32 g, 82.9 mmol) which was used instead of n-butyllithium (1.6 M hexane solution, 34.5 mL, 55.2 mmol) were added. The reaction was allowed to proceed at room temperature for 12 hours, followed by the same post-treatment operation as performed in Example 1, to give 2,4-bis(2,2,2-trifluoroethoxy)-5-(trifluoromethyl)pyrimidine (3) (7.62 g, 22.2 mmol, yield=96%) as a colorless liquid.

Example 7

Preparation of 2,4-bis(2,2,2-trifluoroethoxy)-5-(trifluoromethyl)pyrimidine (3)

To the same reactor as used in Example 5, 2,2,2-trifluoroethanol (6.13 g, 61.3 mmol) and potassium hexamethyldisilazide (1M tetrahydrofuran solution, 64.5 mL, 64.5 mmol) which was used instead of n-butyllithium (1.6 M hexane solution, 34.5 mL, 55.2 mmol) were added. The reaction was allowed to proceed at 0° C. for 18 hours, followed by the same post-treatment operation as performed in Example 1, to give 2,4-bis(2,2,2-trifluoroethoxy)-5-(trifluoromethyl)pyrimidine (3) (6.90 g, 20.1 mmol, yield=87%) as a colorless liquid.

Example 8

Preparation of 2-benzyloxy-4-chloro-5-(trifluoromethyl)pyrimidine (4)

[Formula 4]

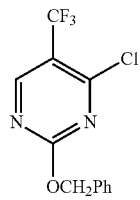

(4)

Placed to a 50 mL eggplant-shaped flask equipped with a stirrer bar, benzyl alcohol (0.50 g, 4.61 mmol) and tetrahydrofuran (4 mL) were added under nitrogen stream. After cooling to −20° C., n-butyllithium (1.6 M hexane solution, 2.88 mL, 4.61 mmol) was added, followed by stirring at the same temperature for 30 minutes.

Hexane (8 mL) was subsequently added and, after cooling to −80° C., 2,4-dichloro-5-(trifluoromethyl)pyrimidine (CFP, 1.00 g, 4.61 mmol) was added. The reaction mixture was followed by further stirring at the same temperature for 30 minutes and then by stirring at room temperature for 2 hours.

After the reaction was completed, the reactant was quenched with saturated aqueous ammonium chloride solution (10 mL), concentratded under reduced pressure, extracted with dichloromethane (10 ml×3 times), combined organic layers and dried them over sodium sulfate, filtrated, and then concentrated to give a crude product of 2-benzyloxy-4-chloro-5-(trifluoromethyl)pyrimidine (4) as a pale yellow solid (1.41 g). At this stage, the conversion of CFP and yield of the product were determined by $^{19}$F-NMR of the crude product using hexafluorobenzene as an internal standard, and it was found that the conversion was 100%, the yield was 90%, and 2-chloro-4-benzyloxy-5-(trifluoromethyl)pyrimidine as a by-product was contained in an amount of 10% a yield.

Furthermore, purification of the crude product by recrystallization using ethylbenzene gave purified 2-benzyloxy-4-chloro-5-(trifluoromethyl)pyrimidine (4) as a white solid (1.00 g, yield=75%, purity=99%).

$^1$H-NMR (CDCl$_3$, 400 MHz) δ 8.70 (d, J=0.8 Hz, 1H), 7.50-7.45 (m, 2H), 7.40-7.32 (m, 3H), 5.50 (s, 2H).

$^{19}$F-NMR (CDCl$_3$, 376 MHz) δ −63.62.

$^{13}$C-NMR (CDCl$_3$, 100 MHz) δ 165.94, 161.08, 158.70 (q, J=5.0 Hz), 135.05, 128.75, 128.57, 122.31 (q, J=270.0 Hz), 117.50 (q, J=33.8 Hz), 70.95.

GC-MS (m/z): 288 (M$^+$, 31), 253 (35), 182 (27), 107 (66), 91 (100).

Element Analysis

Calculated: carbon (49.93%), hydrogen (2.79%), nitrogen (9.70%)

Measured: carbon (19.80%), hydrogen (2.80%), nitrogen (9.68%)

Comparative Example 1

Preparation of 2-benzyloxy-4-chloro-5-(trifluoromethyl)pyrimidine (4)

A crude product of 2-benzyloxy-4-chloro-5-(trifluoromethyl)pyrimidine (4) was obtained in the form of a pale yellow oily product (1.47 g) by performing the same procedures as those in Example 1, except that the amount of tetrahydrofuran (which was 4 mL in Example 8) was changed to 12 mL and that hexane (8 mL) was not used. As a result of $^{19}$F-NMR measurement using hexafluorobenzene as an internal standard, it was found that the conversion was 99%, the yield was 72%, and 2-chloro-4-benzyloxy-5-(trifluoromethyl)pyrimidine as a by-product was contained in an amount of 27% in a yield.

Comparative Example 2

Preparation of 2-benzyloxy-4-chloro-5-(trifluoromethyl)pyrimidine (4)

A crude product of 2-benzyloxy-4-chloro-5-(trifluoromethyl)pyrimidine (4) was obtained in the form of a pale yellow oily product (1.16 g) by performing the same procedures as those in Example 1, except that the amount of tetrahydrofuran (which was 4 mL in Example 8) was changed to 2 mL and that the amount of hexane (which was 8 mL in Example 8) was changed to 20 mL. As a result of $^{19}$F-NMR measurement using hexafluorobenzene as an internal standard, it was found that the conversion was 45%, the yield was 40%, and 2-chloro-4-benzyloxy-5-(trifluoromethyl)pyrimidine as a by-product was contained in an amount of 5% in a yield.

Example 9

Preparation of 2-benzyloxy-4-chloro-5-(trifluoromethyl)pyrimidine (4)

To a 50 mL eggplant-shaped flask equipped with a stirrer bar, benzyl alcohol (0.70 g, 6.45 mmol) and tetrahydrofuran (3 mL) were added under nitrogen stream. After cooling to −20° C., n-butyllithium (1.6 M hexane solution, 3.02 mL, 4.81 mmol) was added, followed by stirring at the same temperature for 30 minutes.

Hexane (10 mL) was subsequently added and, after cooling to −80° C., 2,4-dichloro-5-(trifluoromethyl)pyrimidine (1.00 g, 4.61 mmol) was added. This was followed by further stirring at the same temperature for 30 minutes, and by stirring at 0° C. for 16 hours.

After the reaction was completed, the reactant was quenched with saturated aqueous ammonium chloride solution (10 mL), concentrated under reduced pressure, extracted with dichloromethane (10 ml×3 times), combined organic layers and dried them over sodium sulfate, filtrated, and then concentrated to give a crude product of 2-benzyloxy-4-chloro-5-(trifluoromethyl)pyrimidine (4) as a pale yellow solid (1.43 g). At this stage, the conversion of CFP and yield of the product were determined by $^{19}$F-NMR of the crude product using hexafluorobenzene as an internal standard, it was found that the conversion was 100%, the yield was 93%, and 2-chloro-4-benzyloxy-5-(trifluoromethyl)pyrimidine as a by-product was contained in an amount of 7% in a yield.

Example 10

Preparation of 2-benzyloxy-4-chloro-5-(trifluoromethyl)pyrimidine (4)

To a 50 mL eggplant-shaped flask equipped with a stirrer bar, sodium hydride (60% in oil, 0.20 g, 4.99 mmol) and tetrahydrofuran (8 mL) were at room temperature under nitrogen stream and were stirred for 30 minutes. To the mixture, benzyl alcohol (0.60 g, 5.53 mmol) was added, followed by stirring at the same temperature for 30 minutes. Hexane (20 mL) was subsequently added and, after cooling to −20° C., 2,4-dichloro-5-(trifluoromethyl)pyrimidine (1.00 g, 4.61 mmol) was added and then stirred at the same temperature for 24 hours.

After the reaction was completed, the reactant was quenched with saturated aqueous ammonium chloride solution (10 mL), concentrated under reduced pressure, extracted with dichloromethane (10 mL×3 times), combined organic layers and dried them over sodium sulfate, filtrated, and then concentrated gave a crude product of 2-benzyloxy-4-chloro-5-(trifluoromethyl)pyrimidine (4) as a pale yellow solid (1.62 g). At this stage, the conversion of CFP and yield of the product were determined by $^{19}$F-NMR of the crude product using hexafluorobenzene as an internal standard, and it was found that the conversion was 100%, the yield was 91%, and 2-chloro-4-benzyloxy-5-(trifluoromethyl)pyrimidine as a by-product was contained in an amount of 9% in a yield.

Example 11

Preparation of 2-benzyloxy-4-chloro-5-(trifluoromethyl)pyrimidine (4)

To a 50 mL eggplant-shaped flask equipped with a stirrer bar, benzyl alcohol (0.55 g, 5.07 mmol) and tetrahydrofuran (2 mL) were added under nitrogen stream. After cooling to −40° C., potassium hexamethyldisilazide (1.0 M tetrahydrofuran solution, 4.70 mL, 4.70 mmol) was added, followed by stirring at the same temperature for 30 minutes.

Hexane (15 mL) was subsequently added, and 2,4-dichloro-5-(trifluoromethyl)pyrimidine (1.00 g, 4.61 mmol) was then added. The mixture was followed by further stirring at the same temperature for 30 minutes and then by stirring at −20° C. for 36 hours.

After the reaction was completed, the reaction mixture was quenched with saturated aqueous ammonium chloride solution (10 mL), concentrated under reduced pressure, extracted with dichloromethane (10 mL×3 times), combined organic layers and dried them over sodium sulfate, filtrated, and then concentrated gave a crude product of 2-benzyloxy-4-chloro-5-(trifluoromethyl)pyrimidine (4) as a pale yellow solid (1.45 g). At this stage, the conversion of CFP and yield of the product were determined by $^{19}$F-NMR of the crude product using hexafluorobenzene as an internal standard, and it was found that the conversion was 98%, the yield was 95%, and 2-chloro-4-benzyloxy-5-(trifluoromethyl)pyrimidine as a by-product was contained in an amount of 3% in a yield.

Example 12

Preparation of 2-chloro-4-phenylthio-5-(trifluoromethyl)pyrimidine (8)

[Formula 8]

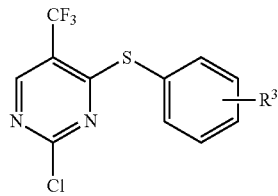

(8)

Placed to a 50 mL eggplant-shaped flask equipped with a stirrer bar, benzenethiol (0.51 g, 4.63 mmol) and tetrahydrofuran (20 mL) were added under nitrogen stream. After cooling to −20° C., n-butyllithium (1.6 M hexane solution, 2.88 mL, 4.61 mmol) was added, followed by stirring at the same temperature for 30 minutes.

2,4-dichloro-5-(trifluoromethyl)pyrimidine (1.00 g, 4.61 mmol) was subsequently added. This was followed by further stirring at the same temperature for 30 minutes and then by stirring at room temperature for 16 hours.

After the reaction was completed, the reaction mixtute was quenched with saturated aqueous ammonium chloride solution (10 mL), concentrated under reduced pressure, extracted with dichloromethane (10 mL×3 times), combined organic layers and dried them over sodium sulfate, filtrated, and then concentrated gave a crude product of 2-chloro-4-phenylthio-5-(trifluoromethyl)pyrimidine (8) as a white solid (1.38 g). At this stage, the conversion of CFP and yield of the product were determined by $^{19}$F-NMR of the crude product using hexafluorobenzene as an internal standard, it was found that the conversion was 99%, the yield was 92%, and 2-phenylthio-4-chloro-5-(trifluoromethyl)pyrimidine as a by-product was contained in an amount of 6% in a yield.

Furthermore, purification of the crude product by recrystallization using ethylbenzene to obtain purified 2-chloro-4-phenylthio-5-(trifluoromethyl)pyrimidine (8) as a white solid (1.13 g, yield=85%, purity=99%).

$^1$H-NMR (CDCl$_3$, 400 MHz) δ 8.54 (d, J=0.8 Hz, 1H), 7.60-7.45 (m, 5H).

$^{19}$F-NMR (CDCl$_3$, 376 MHz) δ −64.32.

$^{13}$C-NMR (CDCl$_3$, 100 MHz) δ 172.75, 163.29, 155.52 (q, J=5.3 Hz), 136.03, 130.72, 129.77, 122.84 (q, J=271.6 Hz), 119.59 (q, J=33.8 Hz).

GC-MS (m/z): 290 (50, M$^+$), 289 (100), 255 (13), 235 (7), 221 (3), 185 (8), 109 (22).

Element Analysis

Calculated: carbon (45.45%), hydrogen (2.08%), nitrogen (9.64%)

Measured: carbon (45.33%), hydrogen (2.08%), nitrogen (9.62%)

Example 13

Preparation of 2-chloro-4-phenylthio-5-(trifluoromethyl)pyrimidine (8)

A crude product (1.27 g) was obtained as a white solid by performing the same procedures as those in Example 12 using the same reactor as that in Example 12, except that the amount of tetrahydrofuran was changed from 20 mL to 10 mL. At this stage, the conversion of CFP and yield of the product were determined by $^{19}$F-NMR of the crude product using hexafluorobenzene as an internal standard, it was found that the conversion was 100%, the yield was 89%, and 2-phenylthio-4-chloro-5-(trifluoromethyl)pyrimidine as a by-product was contained in an amount of 5% in a yield.

Example 14

Preparation of 2-chloro-4-phenylthio-5-(trifluoromethyl)pyrimidine (8)

A crude product (1.21 g) was obtained as a white solid by performing the same procedures as those in Example 12 using the same reactor as that in Example 12, except that sodium hydride (60% in oil, 0.20 g, 4.99 mmol) was used instead of n-butyllithium (1.6 M hexane solution, 2.88 mL, 4.61 mmol) and that the reaction was allowed to proceed at 0° C. for 24 hours. At this stage, the conversion of CFP and yield of the product were determined by $^{19}$F-NMR of the crude product using hexafluorobenzene as an internal standard, it was found that the conversion was 94%, the yield was 84%, and 2-phenylthio-4-chloro-5-(trifluoromethyl)pyrimidine as a by-product was contained in an amount of 8% in terms of yield.

Example 15

Preparation of 2-chloro-4-phenylthio-5-(trifluoromethyl)pyrimidine (8)

A crude product (1.26 g) was obtained as a white solid by performing the reaction procedures as those in Example 12 using the same reaction unit as that in Example 12, except that benzenethiol (0.64 g, 5.79 mmol) was used instead of benzenethiol (0.51 g, 4.63 mmol), that potassium hexamethyldisilazide (1.0 M toluene solution, 4.63 mL, 4.63 mmol) was used instead of n-butyllithium (1.6 M hexane solution, 2.88 mL, 4.61 mmol), and that the reaction was allowed to proceed at −10° C. for 36 hours. At this stage, the conversion of CFP and yield of the product were determined by $^{19}$F-NMR of the crude product using hexafluorobenzene as an internal standard, it was found that the conversion was 98%, the yield was 90%, and 2-phenylthio-4-chloro-5-(trifluoromethyl)pyrimidine as a by-product was contained in an amount of 4% in terms of yield.

INDUSTRIAL APPLICABILITY 2-(2,2,2-trifluoroethoxy)-4-chloro-5-(trifluoromethyl)pyrimidine, 2-benzyloxy-4-chloro-5-(trifluoromethyl)pyrimidine, 2,4-bis(2,2,2-trifluoroethyl)-5-(trifluoromethyl)pyrimidine, and 2-chloro-4-phenylthio-5-(trifluoromethyl)pyrimidine according to the present invention, which are novel, can be used as introducers of a 5-(trifluoromethyl)pyrimidine skeleton and as intermediates for synthesis of various pharmaceuticals and electronic materials.

The invention claimed is:

1. The A 5-(trifluoromethyl)pyrimidine derivative represented by the following Formula 3:

[Formula 3]

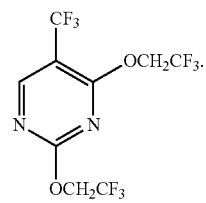

2. A method for producing the 5-(trifluoromethyl)pyrimidine derivative according to claim 1, the method comprising reacting 2,4-dichloro-5-(trifluoromethyl) pyrimidine with a metal 2,2,2-trifluoroethoxide.

3. A method for producing the 5-(trifluoromethyl)pyrimidine derivative according to claim 1, the method comprising reacting 2,4-dichloro-5-(trifluoromethyl) pyrimidine with a metal salt of 2,2,2-trifluoroethanol.

4. The method for producing the 5-(trifluoromethyl)pyrimidine derivative according to claim 3, wherein the metal salt is a lithium salt, a sodium salt, or a potassium salt.

5. The A 5-(trifluoromethyl)pyrimidine derivative represented by the following Formula 4:

[Formula 4]

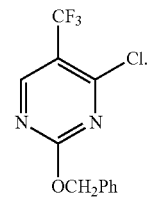

6. A method for producing the 5-(trifluoromethyl)pyrimidine derivative according to claim 5, the method comprising reacting 2,4-dichloro-5-(trifluoromethyl)pyrimidine with a metal salt of benzyl alcohol in a mixed solvent of tetrahydrofuran and hexane.

7. The method for producing the 5-(trifluoromethyl)pyrimidine derivative according to claim 6, wherein the metal salt is a lithium salt, a sodium salt, or a potassium salt.

* * * * *